United States Patent [19]

Ollar

[11] Patent Number: 5,698,414

[45] Date of Patent: *Dec. 16, 1997

[54] METHOD AND APPARATUS FOR TESTING PARAFFINOPHILIC MICROORGANISMS FOR ANTIMICROBIAL AGENT SENSITIVITY

[75] Inventor: Robert-A Ollar, Milford, Pa.

[73] Assignee: Infectech, Inc., Sharon, Pa.

[*] Notice: The term of this patent shall not extend beyond the expiration date of Pat. No. 5,569,592 and 5,316,918.

[21] Appl. No.: 538,899

[22] Filed: Oct. 4, 1995

Related U.S. Application Data

[60] Continuation-in-part of Ser. No. 900,275, Jun. 8, 1992, Pat. No. 5,569,592, which is a division of Ser. No. 841,937, Feb. 25, 1992, Pat. No. 5,316,918, which is a continuation-in-part of Ser. No. 426,573, Oct. 24, 1989, Pat. No. 5,153,119.

[51] Int. Cl.$^6$ ............................ C12Q 1/04; C12N 1/26
[52] U.S. Cl. ........................ 435/34; 435/30; 435/248
[58] Field of Search ........................ 435/30, 34, 36, 435/40, 287.9, 288.1, 288.3, 801, 863, 248

[56] References Cited

U.S. PATENT DOCUMENTS

| | | | |
|---|---|---|---|
| 3,826,717 | 7/1974 | Gilbert et al. | 195/103.5 R |
| 5,153,119 | 10/1992 | Ollar | 435/34 |
| 5,316,918 | 5/1994 | Ollar | 435/34 |
| 5,569,592 | 10/1996 | Ollar | 435/32 |

OTHER PUBLICATIONS

Heifets, et al., *Antimicrobial Agent and Chemotherapy*, 1298–1301 (1989).

Ollar, et al., *Tubercle*, 71, pp. 23–28 (1990).

Fuhs, G. W., *Arch Microbial*, 39, 380–385 German, 1961.

Mishra, et al., *Mycopathologia et Mycologia Applicata*, vol. 51 (2–3), pp. 147–157, (1973).

Ollar, et al., *Zbl. Bakt. Hyg., I.Abt. Orig.*, A234, 81–90 (1976).

Kirhara, et al., *Journal of Clinical Microbiology*, pp. 841–845 (1985).

Gonzales, et al., *Diagn, Microbiol Infect. Dis.*, 8:69–77 (1987).

Wallace, et al., *Chest*, 93 (5) 926–932 (1988).

*Primary Examiner*—Ralph Gitomer
*Attorney, Agent, or Firm*—David V. Radack; Eckert Seamans Cherin & Mellott, LLC

[57] ABSTRACT

A method of determining the sensitivity of at least one paraffinophilic microorganism from a specimen obtained from a patient to different antimicrobial agents and predetermined quantities thereof includes providing at least one receptacle containing an aqueous solution and then inoculating the solution with the specimen. The method then includes placing into the receptacle (i) a paraffin coated slide to bait the at least one paraffinophilic microorganism and (ii) a predetermined quantity of an antimicrobial agent to be tested. The slide is then observed for paraffinophilic microorganism growth or lack thereof to determine whether the predetermined quantity of the antimicrobial agent is effective in inhibiting growth of the paraffinophilic microorganisms on the slide. An associated apparatus is also provided.

3 Claims, 2 Drawing Sheets

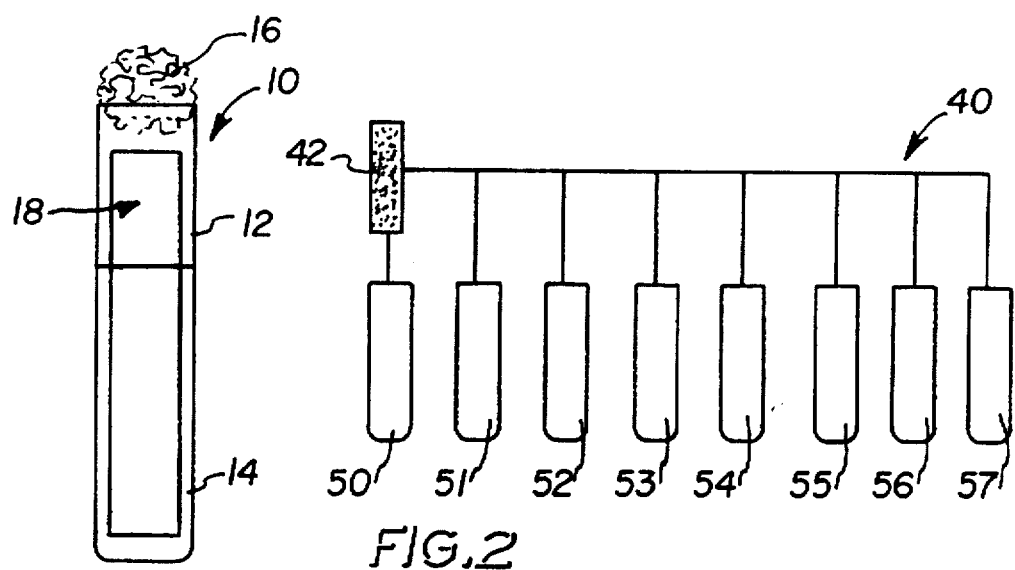
FIG. 1
FIG. 2
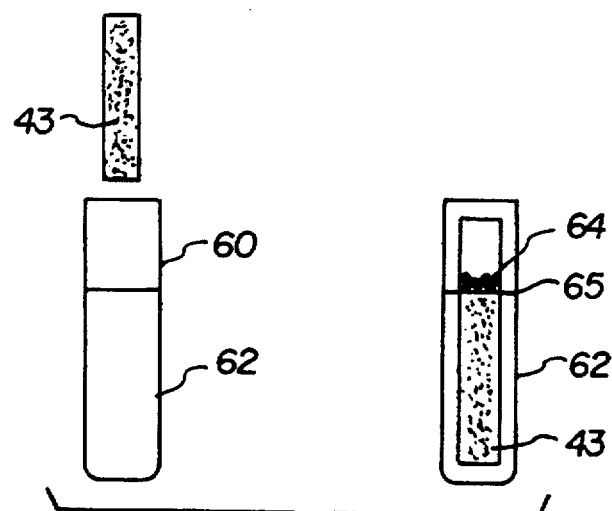
FIG. 3
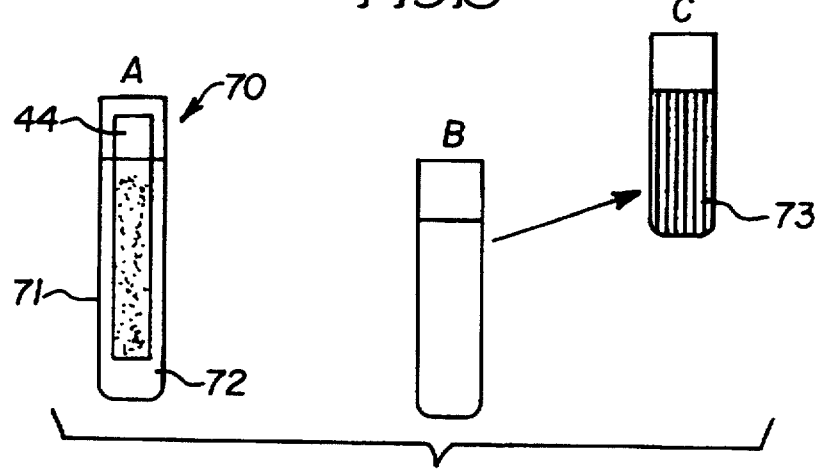
FIG. 4

METHOD AND APPARATUS FOR TESTING PARAFFINOPHILIC MICROORGANISMS FOR ANTIMICROBIAL AGENT SENSITIVITY

CROSS-REFERENCE TO RELATED APPLICATIONS

This application is a continuation-in-part of U.S. patent application Ser. No. 07/900,275 filed Jun. 18, 1992 now U.S. Pat. No. 5,569,592, which was a divisional of U.S. patent application Ser. No. 07/841,937 filed Feb. 25, 1992 now U.S. Pat. No. 5,316,918, which in turn was a continuation-in-part of U.S. patent application Ser. No. 07/426,573 filed Oct. 24, 1989 now U.S. Pat. No. 5,153,119.

BACKGROUND OF THE INVENTION

This invention relates to a method and apparatus for testing paraffinophilic microorganisms for antimicrobial agent sensitivity.

Identifying and treating opportunistic infections very often involves educated guesses as to the nature of the microorganism involved and, once identified, the quantity of antimicrobial agent needed to effectively treat the microorganism. Some antimicrobial agents are extremely expensive, so it would be beneficial to use only that amount necessary to treat the infection. Furthermore, and more importantly, antimicrobial agents can have undesired side effects, so it is prudent to use only that amount needed to effectively treat the infection. Unfortunately, however, there is presently no method by which a physician may rapidly ascertain which antimicrobial agent will work best in order to assure effective inhibition of the growth of the microorganism. This has the consequence of greater expense, less efficacy and the potential for more damaging side effects. This state of affairs exists because medical care givers frequently do not have the type of information regarding antimicrobial agent sensitivity that would make a more exact selection of an antimicrobial agent possible and, once an appropriate antimicrobial agent is selected, facilitate a more precise concentration for use.

It is known that many atypical Mycobacteria grow on basal salt media devoid of any carbon sources other than paraffin wax which is introduced into the media in the form of paraffin wax coated rods. Fuhs, G. W., "Der Mikrobielle Abbau Von Kohlenwasserstoffen", *Arch. Mikrobiol.*, 39:374-422 (1961). Mishra, S. K. et al., "Observations On Paraffin Baiting As A Laboratory Diagnostic Procedure In Nocardiosis", *Mycopathologica And Mycologia Applicata*, 51 (2-3):147-157 (1973) utilized paraffin coated rods and basal salt medium to isolate *Nocardia asteroides* from clinical specimens such as sputum, bronchial lavage and cerebrospinal fluid.

The technique was further improved by substituting paraffin wax coated slides for rods and thereby making possible the use on an in situ Kinyoun cold acid-fastness staining procedure for organisms growing on the paraffin coated slides. Ollar, R. A., "A Paraffin Baiting Technique That Enables A Direct Microscopic View of "in situ" Morphology Of *Nocardia asteroides* With The Acid-Fast Or Fluorescence Staining Procedures", *Zbl. Bakt. Hyg., Abt. Orig. A*, 234:81-90 (1976). With this assay, a positive reaction tells the user immediately that a mycobacteria organism other than *M. tuberculosis* is present.

As for antimicrobial sensitivity testing, U.S. Pat. No. 3,826,717 provides an antibiotic sensitivity test container which includes a plurality of wells which contain a solid nutrient media. The wells are positioned in rows with each row containing a single antibiotic and different wells within the row having different concentrations. A control well is provided which contains no antibiotic but the media.

Despite the above teachings, however, there still remains a need for efficient and economical method and an inexpensive apparatus for testing paraffinophilic microorganisms for antimicrobial agent sensitivity.

SUMMARY OF THE INVENTION

The invention has met or surpassed the above-mentioned need as well as others. The method of determining the sensitivity of at least one paraffinophilic microorganism from a specimen obtained from a patient to different antimicrobial agents and predetermined quantities thereof includes providing at least one receptacle containing an aqueous solution and then inoculating the solution with the specimen. The method then includes placing into the receptacle (i) a paraffin coated slide to bait the at least one paraffinophilic microorganism and (ii) a predetermined quantity of an antimicrobial agent to be tested. The slide is then observed for paraffinophilic microorganism growth or lack thereof to determine whether the predetermined quantity of the antimicrobial agent is effective in inhibiting growth of the paraffinophilic microorganisms on the slide.

An associated apparatus is also provided that includes a receptacle adapted to contain an aqueous solution, an amount of antimicrobial agent to be tested and the patient specimen and a paraffin coated slide adapted to being placed in said receptacle. In this way, observation of the growth of the paraffinophilic microorganisms from the specimen on the slide can be used to determine the concentration of the antimicrobial agent necessary to resist paraffinophilic microorganism growth on the slide.

BRIEF DESCRIPTION OF THE DRAWINGS

FIG. 1 shows a schematic front elevational view of a test tube holding the paraffin coated slide in a sterile aqueous solution inoculated with *Mycobacterium avium-intracellulare* ("MAI").

FIG. 2 shows a schematic view of the acid-alcohol fastness assay.

FIG. 3 shows the tellurite reduction assay.

FIG. 4 shows the nitrate reduction assay.

DESCRIPTION OF THE PREFERRED EMBODIMENTS

Figure 5:
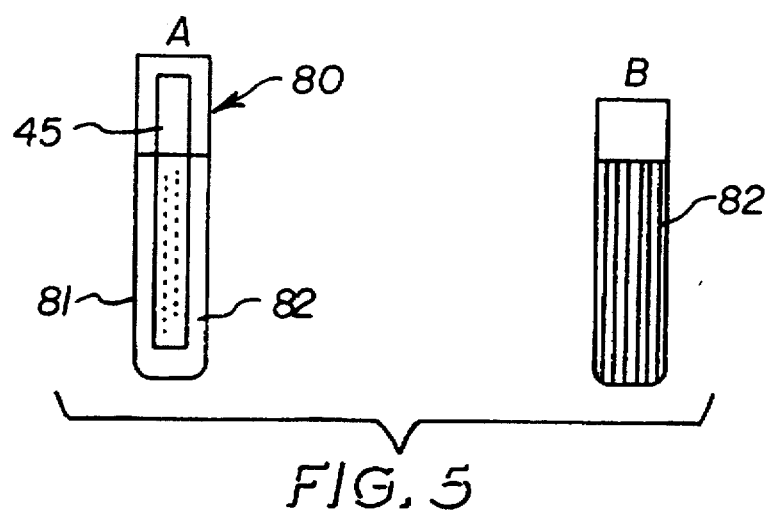
FIG. 5 shows the urea hydrolysis assay.

When referred to herein, the term "atypical Mycobacteria" means all mycobacteria other than *M. tuberculosis*, *M. leprae*, and *M. paratuberculosis*.

As used herein, the term "patient" refers to a member of the animal kingdom including human beings, whose body specimen is being processed by the method and apparatus of the invention.

Referring to FIG. 1, part of the MAI isolation and speciation kit 10 is shown. FIG. 1 shows a standard test tube 12 which contains a sterile aqueous solution 14 (such as Czapek broth) and a cotton plug 16 to seal the tube 12. In use, the specimen to be tested for the presence or absence of MAI is introduced into the test tube 12 and the paraffin coated slide 18 is subsequently analyzed. The specimen can be an amount of a patient's blood, stool or sputum. The latter two specimens can be directly inoculated into the MAI isolation and speciation kit without the need for some sort of hemoculture broth.

Preferably, the slides 18 are prepared by first cutting standard microscope slides longitudinally so that they fit into the test tubes 12 and so they can be easily withdrawn. The test tubes 12 are plugged and sterilized by autoclaving.

The paraffin coating on the slides is preferably accomplished by first melting several tubes of sterilized histological grade paraffin embedding wax in a boiling water bath, while separately, a glass petri dish containing a slide support is heated on an electric hot plate to a temperature sufficient to keep the paraffin molten. The molten paraffin was is then poured into the heated petri dish to a level sufficient to cover the slide on the support.

Ethanol-flame sterilized forceps are preferably used to transfer a previously uncoated slide onto the slide support in the heated petri dish which contains the molten wax. The slide is immersed in the molten wax for a few seconds such that it is covered by a thin coat of paraffin wax. A plurality of slides are prepared in this same fashion, with a tube of molten paraffin wax added after 6–10 slides have been prepared to ensure that there is always sufficient wax to cover the supported slides.

The Czapek broth 14 can be provided with an antibacterial and antifungal/antibiotic cocktail such as that sold under the trade name "PANTA" made by Becton Dickenson/Johnston Labs Division. This product will resist possible contaminating factors such as *Pseudomonas aeruginosa* or *Candida tropicalis*. This product has no effect on the MAI since the MAI is resistant to the currently used antibiotics in "PANTA".

The kit 10 can also serve as a means of distinguishing between atypical Mycobacteria and nocardioform organisms on the one hand and *Mycobacterium tuberculosis* on the other hand because the latter cannot utilize paraffin wax as a sole source of carbon. As is known, a tropism is created between the paraffin and organism capable of using the paraffin as its carbon source, such as atypical Mycobacteria and nocardioform organisms. The outward manifestation of this tropism or baiting is the appearance of growth on the paraffin surface.

Once it is determined that Mycobacteria other than *Mycobacterium tuberculosis* or a nocardioform organism is present on the slide, an alcohol-acid fastness test 40 (FIG. 2) can be used to further distinguish between the atypical Mycobacteria and the nocardioform organisms. As is known, atypical Mycobacteria are alcohol-acid fast; nocardioform organisms are acid-fast and *Pseudomonas aeruginosa* or *Candida tropicalis* are neither acid nor alcohol-acid fast. Thus, these latter two groups (nocardioforms and *Pseudomonas aeruginosa* or *Candida tropicalis*) can be eliminated as possibilities by the alcohol-acid fastness testing kit 40.

Referring to FIG. 2, the acid-alcohol fastness testing means 40 is shown. This testing means 40 includes a plurality of test tubes containing different solutions. The solutions stain the MAI on the slide for subsequent analysis under a microscope.

The paraffin coated slide culture with visible MAI growth 42 is removed from the test tube 12 of FIG. 1 and is first immersed in two consecutive tubes of distilled water 50, 51 and then immersed in a tube of Kinyoun carbolfuchsin 52 for fifteen minutes. The slide 42 is again immersed in a tube of distilled water 53 and then placed in a tube 54 containing acid-alcohol consisting of 97 ml absolute ethanol and 3.0 ml concentrated HCl for five minutes. After this, the slide is washed in a fourth tube of distilled water 55 and then placed into a tube 56 of 1.0% (v/v) aqueous Methylene blue solution for one minute. Finally, the slide is washed in a fifth tube 57 of distilled water.

The slide culture is then removed from the fifth tube 57 of distilled water and blotted gently with a clean absorbent paper tissue. The slide culture is then viewed under a microscope at 250×, 450× and 1000× oil immersion.

FIG. 3 shows the tellurite reduction assay which consists of a test tube 60 filled, preferably, with a Czapek broth plus an amount of potassium tellurite reagent 62. A cultured slide 43 is immersed into the test tube 60 and incubated. If MAI is present on the slide, a heavy black precipitate 64 forms at the level of the meniscus pellicle 65 of the slide 43. This test alerts the user to the possibility of MAI presence. MAI presence can be confirmed after the assay results are known for the assays discussed hereinafter.

FIG. 4 shows the nitrate reduction assay 70. A slide culture 44 showing heavy growth is assayed for the ability to reduce nitrates to nitrites. This is done by adding nitrates to a tube 71 containing a sterile broth. After a period of 12–24 hours incubation at 37° C., the slide 44 is removed from the sterile nitrate broth 72 and five drops of sulfanilic acid reagent solution followed by five drops of alpha naphthylamine reagent solution are added to the tubes 71. The reduction of nitrate to nitrite appears as a red colored broth 73. As is known, if the nitrate is reduced to nitrite, this indicates the absence of MAI on the slide.

FIG. 5 shows the urea hydrolysis reaction assay 80. A slide culture 45 is added to a plugged tube 81 containing 4.5 ml of sterile urea broth 82. The culture is incubated at 37° C. and checked after a period of three days. A positive reaction involves a color change of the broth 82 to pink or red after a period of three days. As is known, if the solution changes color, this indicates the absence of MAI on the slide 45.

Figure 6:
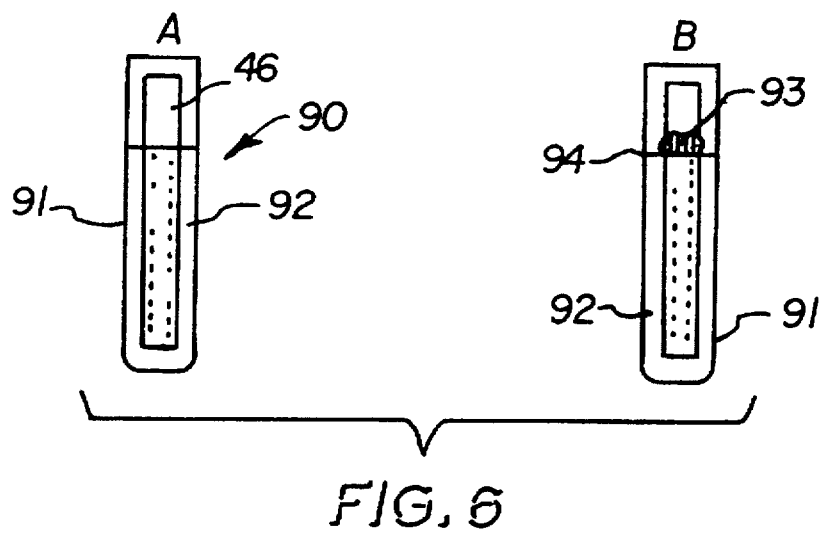
FIG. 6 shows the Tween 80 hydrolysis assay.

FIG. 6 shows the emulsifier hydrolysis assay 90. The emulsifier used is "Tween 80", a trademark of Atlas Chemical Industries, Inc. and is generically described as polyoxyethylene derivatives of fatty acid partial esters of sorbitol anhydrides. A slide culture 46 was added to sterile plugged tubes 91 containing Tween 80 media 92 and incubated at 37° C. A positive reaction involved the appearance of a red coloration 93 on the meniscus pellicle 94 of the slide 46 within five days. As is known, the presence of the red coloration in the slide indicates the absence of MAI on the slide.

It will be appreciated that at least one of the MAI identification tests (tellurite reduction, nitrate reduction, urea hydrolysis or "Tween 80" hydrolysis) should be performed, with the tellurite reduction test being the most important of the four tests. Preferably, all four of the tests should be performed in order to more accurately speciate and identify MAI.

Figure 7:
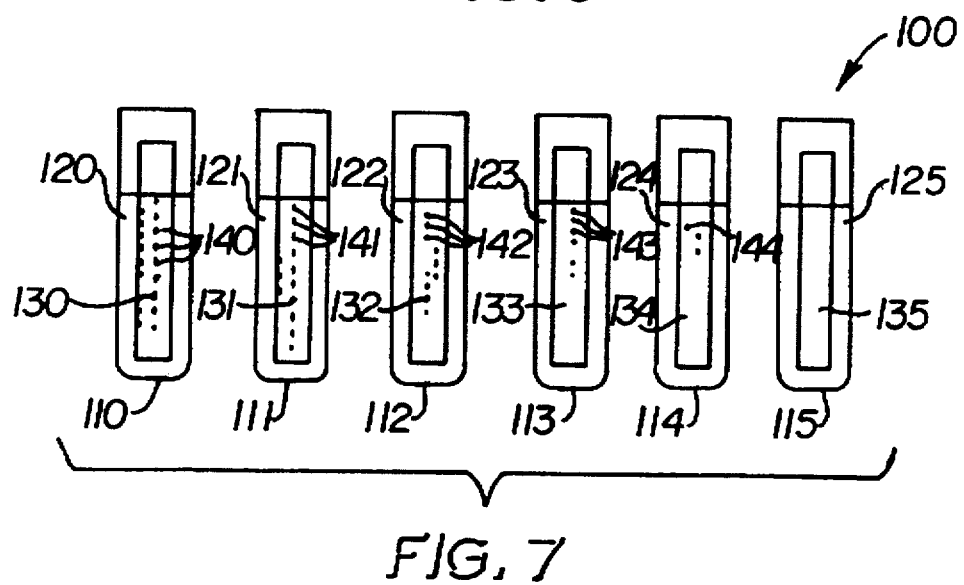
FIG. 7 shows the antimicrobial agent sensitivity testing assay of the invention.

FIG. 7 shows the antimicrobial agent sensitivity testing assay 100 of the invention. This method and the associated apparatus tests the sensitivity of the MAI to different antimicrobial agent and/or dosages of antimicrobial agent. The assay consists of preferably six tubes 110–115 each containing an amount of Czapek broth solution 120–125 and an amount of a specimen containing MAI to be tested. Broth solutions 121–125 contain uniform intervals of increasing concentration of an antimicrobial agent to be tested. Broth 120 does not contain an amount of the antimicrobial agent as this tube 110 will be the "control" tube. Tube 110, preferably, contains an amount of saline.

Paraffin slide cultures 130–135 were prepared as was discussed hereinbefore. Each of these slide cultures 130–135 are introduced into their respective tubes 110–115. The tubes 110–115 with slide cultures 130–135 are then incubated at 37° C. and checked at six days, seven days, eight days and ten days. By observing the MAI growth 140–144 on the paraffin surfaces of each of the slide cultures 130–135, the minimal inhibitory concentration ("MIC") of antimicrobial agent necessary to prevent MAI growth on the paraffin culture slides 130–135 can be determined. In the case of FIG. 7, the MIC concentration is found in tube 115 because there is no MAI growth on slide 135.

As can be appreciated, the method and apparatus of the invention provide an efficient, effective and economical way of determining the sensitivity of MAI to different antimicrobial agents and predetermined quantities thereof. The invention, however, is not limited to MAI but can also be effective for any paraffinophilic microorganism. As used herein, the term "paraffinophilic" means an organism that can employ paraffin wax as a source of carbon in a basal salt media, devoid of other forms of carbon. The organism can be bacterial or fungal in nature.

It will be appreciated that although apparatus 50 is shown with multiple receptacles and multiple slides 80–85, that the invention is not limited to multiple receptacles and multiple slides, but covers also a single receptacle and a single slide.

The method of the invention can be used to determine the antibiotic sensitivity of at least one of the paraffinophilic microorganisms selected from the group consisting of Micrococcus Paraffinae; Corynebacterium Simplex; Ahnl; Mycococcus (Rhodococcus) Cinnabareus; Ahnl. Mycococcus (Rhodoc) Rhodochrous; Mycobact. Perrugosum Var. Athanicum; Mycobact. Rubrum Var. Propanicum; Mycobacterium Hyalinum; Mycobacterium Lacticola; Mycobacterium Album, M. Luteum; Mycobacterium Microti; Mycobacterium Rubrum, Mycobacterium Phlei.; Mycobacterium Phlei, M. Smegmatis; Mycobacterium Testudo; Mycobacterium-Avium-Intracellulare; Nocardia Spp.; Actinomyces; Candida Lipolytica; Candida Tropicalis, Torulopsis Colliculosa; Monila Sp., Hansenula Sp., Torula rossa; Penicillium Sp.; IHNL Aspergillus Flavus; Aspergillus sp., Penicillium Sp.; Citromyces Sp., Scopulariopsis Sp.; Pseudomonas Fluorescens Liquefaciens; Ahnl, Pem. Fluorescens Denitrificans; Pseudomonas Aeruginosa.

It will be appreciated that in clinical medical practice, there are situations both where a patient has a single paraffinophilic microorganism (such as MAI) or where another patient may have multiple paraffinophilic microorganisms (such as MAI and *Mycobacterium Kansasii*). It is imperative that all paraffinophilic microorganisms be treated as each one is probably causing pathogenicity in the patient. Thus, if an immunocompromised patient has a lung, liver or kidney abscess, the physician is interested in the antimicrobial agent that will inhibit all bacterial growth on the slide, whether or not that bacterial growth involves one or multiple paraffinophilic microorganisms.

EXPERIMENTAL RESULTS

A. Materials

1. Strains

Strains of MAI used in the following experiments were originally isolated from AIDS patients at St. Vincent's Hospital and Medical Center of New York and at Memorial Sloan-Kettering Cancer Center. The strains from both institutions were identified by routine morphologic and microbiological procedures with confirmation by DNA hybridization (Gene Probe Kit: Biogen) for *M. avium* and *M. intracellulare*. Strains isolated at St. Vincent's Hospital were 10,000; 1762; 1516; 15113; 8515; 6475; 5097; 8197; and 4861. Those from Memorial Sloan-Kettering Cancer Center were SK015; SK016; SK095; SK069; SK034; SK060; and SK024. All strains were isolated from patients with AIDS and identified as *M. avium* species with the exception of SK069 which was an *M. intracellulare* isolated from an immunocompetent patient with cavitary pulmonary disease.

2. Antimicrobial Agents

Stock solutions of chemotherapeutic agents were prepared. Amikacin (Bristol-Myers) was dissolved in distilled water and filter-sterilized; azithromycin (Pfizer) was dissolved in 95% ethanol and filter-sterilized; and ciprofloxacin (Miles Laboratories) was dissolved in distilled water and filter-sterilized.

B. Paraffin Slide Culture Assay

A paraffin slide culture assay for antibiotic sensitivity in accordance with the method of the invention and done with apparatus described and shown in FIG. 7 was performed on the strains described above in connection with the antimicrobial agents also described above.

Standard microscope slides were longitudinally cut, sterilized, and coated with a thin layer of Paraplast compound (histological grade paraffin wax plus plastic polymers—Monoject Scientific Division of Sherwood Medical, St. Louis, Mo. 63103, USA). The best paraffin wax coatings were those that were extremely thin. This was achieved by quickly dipping the slide into molten paraffin wax and rapidly removing it from same. When a paraffin wax coating was too thick, the wax layer often sloughed off after prolonged incubation at 37° C. After the coating process, the slides were stored in sterile cotton-plugged tubes until needed.

1. Ciprofloxacin—HCL

Using the apparatus of FIG. 7, into each of the tubes 111–115 was introduced 0.5 ml of infectious inoculum, the initial working antimicrobial solution, the paraffin coated slides 131–135 and 4.5 ml of Czapek broth. A control tube 110 contained 0.5 ml of infectious inoculum, 0.5 ml of normal saline and 4.5 ml of Czapek broth. The control tube 110 also contained a paraffin coated slide 130. Each tube 111–115 contained increasing antimicrobial agent concentrations with tube 111 containing 3.6 micrograms/ml; tube 112 containing 7.3 micrograms/ml; tube 113 containing 10.9 micrograms/ml; tube 114 containing 14.5 micrograms/ml; and tube 115 containing 18.2 micrograms/ml.

The experiments were done for each of the strains to make up one series of experiments. The same experiments were repeated for a second series. The paraffin control slide cultures in each of the experiments were usually read after 5–10 days incubation of 37° C., with 8 days being the preferred waiting period.

Table One lists the strains and reports the MIC and days of confluency for each strain for each experiment series. The MIC is defined as the lowest concentration of antimicrobial agent necessary to inhibit growth on the slides. The MIC is measured in units of micrograms/ml.

TABLE ONE

| Strains | Exp. Series I | | Exp. Series II | |
|---|---|---|---|---|
| | MIC | Days To Confluency | MIC | Days To Confluency |
| 10,000 | 3.6 | 9 | 3.6 | 7 |
| 1762 | 18.2 | 9 | 14.5 | 8 |
| 1516 | NG* | NG | 3.6 | 8 |
| 15113 | 3.6 | 10 | 3.6 | 9 |
| 8515 | 7.3 | 9 | 7.3 | 8 |
| 6475 | 3.6 | 10 | 7.3 | 9 |
| 5097 | 3.6 | 10 | 7.3 | 8 |
| 8197 | 3.6 | 9 | 3.6 | 8 |
| 4861 | 3.6 | 10 | 3.6 | 8 |
| SK015 | 14.5 | 7 | 14.5 | 6 |
| SK016 | 7.3 | 7 | 7.3 | 6 |
| SK095 | 10.9 | 7 | 7.3 | 6 |
| SK069 | 18.2 | 8 | >18.2 | 7 |
| SK037 | 18.2 | 7 | 14.5 | 7 |
| SK060 | 7.3 | 7 | 7.3 | 7 |
| SK024 | 7.3 | 7 | 3.6 | 6 |

*NG = No Growth.

The basic methodology of the invention was derived from Experimental Series I with ciprofloxacin-HCL. As expected, the control tube showed the greatest amount of growth on the paraffin wax surface. When visible confluent growth on the paraffin slide surface in the control tube occurred, the tubes 111–115 containing varying dilutions or ciprofloxacin were examined. The effects of increased concentration of ciprofloxacin-HCL on MAI growth were clearly visible on the paraffin slides. The concentration of ciprofloxacin in the tube containing the lowest antimicrobial concentration in which there were no visible colonies on the paraffin wax coated slide was defined as the minimal inhibitory concentration ("MIC") for this system. Lack of growth at this concentration was confirmed by microscopic examination of slides stained by the Kinyoun acid-fast staining method. This method was used to determine the MIC in all subsequent series of the antimicrobial sensitivity tests.

There was no statistically significant variation of Series II and III for ciprofloxacin-HCL (normal approximation with continuity correction=0.419 two-tailed p value for normal approximation=0.68). This confirmed the reproducibility of the method between experimental series. The MIC values obtained in these experimental series were quite close to those obtained by other investigators. See, for example, Heifets, L. and Lindholm-Levy, P. "Comparison Of Bactericical Activities Of Streptomycin, Amikacin, Kanamycin And Capreomycin Against *Mycobacterium avium* and *M. tuberculosis*", *Antimicrob. Ag. Chemother,* 1989:33: 1298–1301.

2. Azithromycin Testing

Again using the apparatus of FIG. 7, into each of the tubes 111–115 was introduced 0.5 ml of infectious inoculum, the initial working antimicrobial solution, the paraffin coated slides 131–135 and 4.5 ml of Czapek broth medium. A control tube 110 of azithromycin contained 0.5 ml of 95% ethanol in 4.5 ml Czapek broth and 0.5 ml of infectious inoculum along with slide 130. Each tube 111–115 contained increasing antimicrobial agent concentrations with tube 111 containing 2.6 micrograms/ml; tube 112 containing 5.3 micrograms/ml; tube 113 containing 7.9 micrograms/ml; tube 114 containing 10.6 micrograms/ml; and tube 115 containing 13.2 micrograms/ml.

The experiments were done for each of the strains to make up one series of experiments. The same experiments were repeated for a second series and were repeated again for a third series. The paraffin coated slide culture in each of the experiments were usually read after 5–10 days incubation at 37° C., with 8 days being the preferred waiting period.

Table Two lists the strains and reports the MIC (in micrograms/ml) and days at confluency for each strain for each of the Experimental Series I, II and III.

TABLE TWO

| Strains | EXP. SERIES I | | EXP. SERIES II | | EXP. SERIES III | |
|---|---|---|---|---|---|---|
| | MIC | Days To Confluency | MIC | Days To Confluency | MIC | Days To Confluency |
| 10.000 | 2.6 | 6 | 2.6 | 6 | 2.6 | 6 |
| 1762 | 5.3 | 7 | 2.6 | 6 | 5.3 | 6 |
| 1516 | 2.6 | 8 | 2.6 | 8 | 5.3 | 8 |
| 15113 | 5.3 | 8 | 5.3 | 10 | 2.6 | 6 |
| 8515 | 5.3 | 8 | 2.6 | 6 | 2.6 | 6 |
| 6475 | 2.6 | 8 | 2.6 | 8 | 2.6 | 6 |
| 5097 | 7.9 | 6 | 2.6 | 6 | 5.3 | 6 |
| 8197 | 5.3 | 7 | 2.6 | 6 | 2.6 | 6 |
| 4861 | 5.3 | 10 | 2.6 | 6 | 2.6 | 6 |
| SK015 | 7.9 | 7 | 5.3 | 6 | 5.3 | 7 |
| SK016 | 7.9 | 10 | 10.6 | 6 | 5.3 | 8 |
| SK095 | 2.6 | 7 | 5.3 | 6 | 5.3 | 7 |
| SK069 | 2.6 | 7 | 2.6 | 6 | 5.3 | 8 |
| SK037 | 5.3 | 7 | 7.9 | 6 | 5.3 | 8 |
| SK060 | 2.6 | 7 | 7.9 | 6 | 2.6 | 6 |
| SK024 | 5.3 | 7 | 7.9 | 6 | 2.2 | 7 |

There was no significant variation between experimental series (Friedman Statistic corrected for ties=20.95, p=0.14, sample size=3, df=15).

The values obtained for the MIC for azithromycin were different from values obtained by other researchers. See, e.g., Inderlied, C. B., Kolonoski, P. T., Wu, M. and Young, L. S., "In vitro and in vivo Activity of Azithromycin (CP 62.993) Against the *Mycobacterium avium* Complex", *J. Infect. Dis.*, 1989:159: 994–997. One explanation for this is that azithromycin is very sensitive to pH changes. The above experiments were performed at pH=7.5. At lower pH the azithromycin, which is a macrolide antibiotic, is completely ionized and therefore would have great difficulty in crossing the cytoplasmic membrane. This translates into the need for higher concentrations of azithromycin, thus leading to higher MIC values. Furthermore, there is no accepted standard for antimicrobial sensitivity of MAI to azithromycin.

3. Amikacin Testing

Using the apparatus of FIG. 7, into each tube 110–115 was introduced 0.5 ml of infectious inoculum, the initial working antimicrobial solution, the paraffin coated slides 131–135 and 4.5 ml of Czapek broth medium. Tube 110 is a control tube and did not contain any amikacin but instead contained 0.5 ml of 95% ethanol in 4.5 ml of Czapek broth and 0.5 ml of infectious inoculum along with slide 130. Each tube 111–115 contained increasing amikacin antimicrobial agent concentrations, with tube 111 containing 3.2 micrograms/ml; tube 112 containing 6.4 micrograms/ml; tube 113 containing 9.6 micrograms/ml; tube 114 containing 12.8 micrograms/ml; and tube 115 containing 16 micrograms/ml.

These experiments were done for each of the strains to make on series of experiments. The same experiments were reported for a second series and were repeated again for a third series. The paraffin slide cultures in each of the experiments were usually read after 5–10 days incubation at 37° C., with 8 days being the preferred waiting period.

Table Three lists the strains and reports the MIC and days of confluency for each strain for each.

TABLE THREE

| Strains | EXP. SERIES I | | EXP. SERIES II | | EXP. SERIES III | |
|---|---|---|---|---|---|---|
| | MIC | Days To Confluency | MIC | Days To Confluency | MIC | Days To Confluency |
| 10.000 | >16.0 | 7 | >16.0 | 7 | 3.2 | 5 |
| 1762 | >16.0 | 7 | 12.0 | 7 | 3.2 | 5 |
| 1516 | 6.4 | 8 | 6.4 | 9 | 6.4 | 12 |
| 15113 | 3.2 | 8 | 6.4 | 5 | 3.2 | 6 |
| 8515 | 6.4 | 7 | 3.2 | 5 | 3.2 | 5 |
| 6475 | 12.0 | 7 | 3.2 | 5 | 3.2 | 5 |
| 5097 | NG* | NG | 6.4 | 5 | 6.4 | 5 |
| 8197 | >16.0 | 7 | >16.0 | 7 | 3.2 | 5 |
| 4861 | 12.0 | 8 | 3.2 | 6 | 3.2 | 7 |
| SK015 | 6.4 | 6 | 6.4 | 6 | 3.2 | 5 |
| SK016 | 7.3 | 5 | 9.6 | 6 | 6.4 | 5 |
| SK095 | 3.2 | 5 | 6.4 | 6 | 6.4 | 5 |
| SK069 | 3.2 | 6 | 9.6 | 6 | 6.4 | 6 |
| SK037 | 9.6 | 5 | >16.0 | 6 | 6.4 | 5 |
| SK060 | 6.4 | 5 | 6.4 | 7 | 3.2 | 5 |
| SK024 | 6.4 | 5 | 9.6 | 6 | 3.2 | 5 |

*NG = No Growth.

There was no statistically significant variation of Series I, II and III (Friedman Statistic corrected for ties=14.79, p=0.39, sample step=3, df=14). This confirmed the reproducibility of this test among series. The MIC values obtained in these experimental series were quite close to those obtained by other researchers. See, e.g., Inderlied, C. B., Young, L. S. and Yamanda, J. K., "Determination Of in vivo Susceptibility Of *Mycobacterium avium* Complex Isolates To Antimycobacterial Agents By Various Methods", *Antimicrob. Ag. Chemother,* 1987:32: 1697–1702.

It will be appreciated that the present invention provides a method and apparatus for testing MAI for antimicrobial agent sensitivity. The apparatus is easy to use and inexpensive and the method is accurate and efficient.

Whereas particular embodiments of the invention have been described hereinabove, for purposes of illustration, it will be evident to those skilled in the art that numerous variations of the details may be made without departing from the invention as defined in the appended claims.

What is claimed is:

1. A method of determining the sensitivity of a paraffinophilic microorganism from a specimen obtained from a patient to different antimicrobial agents and predetermined quantities thereof, said method comprising:

providing at least one receptacle containing an aqueous solution;

inoculating said solution with said specimen;

placing into said receptacle (i) a paraffin coated slide to bait said paraffinophilic microorganism and (ii) a predetermined quantity of an antimicrobial agent to be tested; and observing said paraffinophilic microorganism growth or lack thereof on said slide to determine whether said predetermined quantity of said antimicrobial agent is effective in inhibiting growth of said paraffinophilic microorganism on said slide.

2. The method of claim 1, including said paraffinophilic microorganism is selected from the group consisting of *Micrococcus Paraffinae; Corynebacterium Simplex; Ahnl; Mycococcus (Rhodococcus) Cinnabareus; Ahnl. Mycococcus (Rhodoc) Rhodochrous; Mycobact. Perrugosum Var. Athanicum; Mycobact. Rubrum Var. Propanicum; Mycobacterium Hyalinum; Mycobacterium Lacticola; Mycobacterium Album, M. Luteum; Mycobacterium Microti; Mycobacterium Rubrum, Mycobacterium Phlei.; Mycobacterium Phlei, M. Smegmatis; Mycobacterium Testudo; Mycobacterium-Avium-Intracellulare; Nocardia Spp.; Actinomyces; Candida Lipolytica; Candida Tropicalis, Torulopsis Colliculosa; Monila Sp., Hansenula Sp., Torula rossa; Penicillium Sp.; IHNL. Aspergillus Flavus; Aspergillus sp., Penicillium Sp.; Citromyces Sp., Scopulariopsis Sp.; Pseudomonas Fluorescens Liquefaciens; Ahnl, Pem. Fluorescens Denitrificans; Pseudomonas Aeruginosa.*

3. The method of claim 1, including providing a plurality of receptacles each containing an aqueous solution;

inoculating each receptacle with an amount of said specimen;

placing (i) a separate paraffin coated slide and (ii) an amount of an antimicrobial agent to be tested in each receptacle, each said receptacle containing a different predetermined quantity of said antimicrobial agent; and observing said paraffinophilic microorganism growth or lack thereof on said slides to determine a minimum inhibitory concentration of said antimicrobial agent to inhibit growth of said paraffinophilic microorganism.

* * * * *